United States Patent [19]

Hubertus

[11] Patent Number: 4,838,678
[45] Date of Patent: Jun. 13, 1989

[54] MAGNIFYING BINOCULAR OPHTHALMOSCOPE

[75] Inventor: Maximiliaan J. Hubertus, Coolbinia, Australia

[73] Assignee: Lyons Eye Institute of Western Australian Incorporated, Nedlands, Australia

[21] Appl. No.: 130,626

[22] Filed: Dec. 8, 1987

[30] Foreign Application Priority Data

Dec. 10, 1986 [AU] Australia .............................. PH09448

[51] Int. Cl.⁴ .......................... A61B 3/10; G02B 21/20
[52] U.S. Cl. ........................................ 351/205; 350/514
[58] Field of Search ................ 351/205; 350/514, 515, 350/516

[56] References Cited

U.S. PATENT DOCUMENTS

| | | | |
|---|---|---|---|
| 3,464,759 | 9/1969 | Scholer et al. ...................... | 350/515 |
| 3,963,329 | 6/1976 | Stumpf et al. ....................... | 351/205 |
| 4,009,930 | 10/1975 | Abe et al. ............................ | 350/516 |
| 4,015,898 | 4/1977 | Schirmer ............................. | 351/205 |
| 4,449,797 | 5/1984 | Kocher et al. ....................... | 351/205 |
| 4,710,002 | 12/1987 | Pomerentzelt ....................... | 351/205 |

FOREIGN PATENT DOCUMENTS 406782 9/1968 Australia .

Primary Examiner—Rodney B. Bovernick
Assistant Examiner—Ryan
Attorney, Agent, or Firm—Kerkam, Stowell, Kondracki & Clarke

[57] ABSTRACT

A magnifying binocular opthalmoscope comprising a mirror system and a telescopic lens system. Light travels from the source of an image to the mirror system and is reflected thereby to travel through the telescopic lens system. The telescopic lens system comprises two series of lenses to provide the operator of the magnifying binocular opthalmoscope with binocular vision. The operator is able to view a magnification of the image of the source through the eye pieces of the two series of lenses.

4 Claims, 4 Drawing Sheets

MAGNIFYING BINOCULAR OPHTHALMOSCOPE

The present invention relates to a magnifying binocular ophthalmoscope.

In accordance with one aspect of the present invention there is provided a magnifying binocular ophthalmoscope comprising mirror means and lens means arranged such that when an image is viewed by an observer through said ophthalmoscope said image appears as a magnification of the source of the said image.

The invention will now be described, by way of example, with reference to the accompanying drawings in which.

Figure 1:
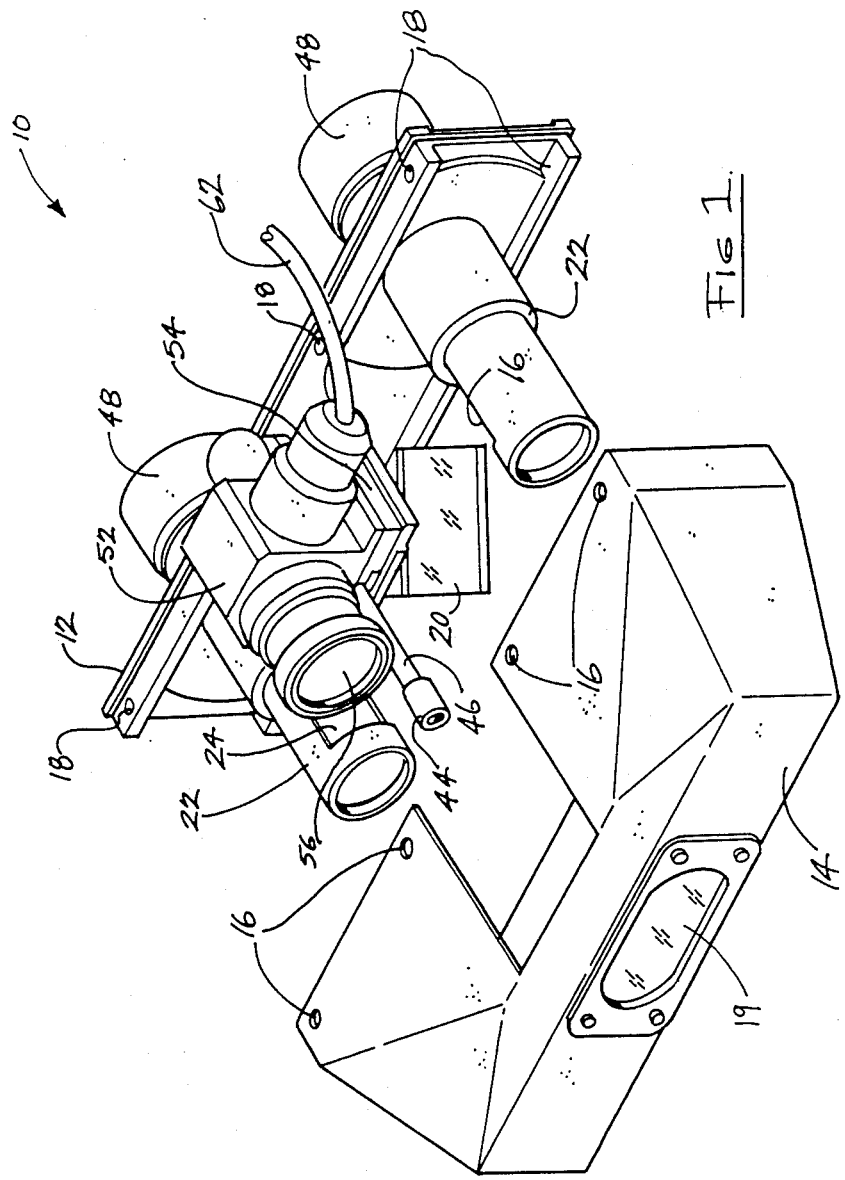
FIG. 1 is a perspective view of the magnifying binocular ophthalmoscope in accordance with the present invention, with the casing cover removed therefrom.

In FIG. 1 there is shown a binocular magnifying ophthalmoscope 10 in accordance with one aspect of the present invention.

The magnifying binocular ophthalmoscope 10 comprises a support frame 12, substantially in the form of a plate, and optical components which are mounted on the support frame 12. A casing cover 14 normally covers the optical components. The cover 14 is attached to the support frame 12 by way of screws (not shown) engaging in the apertures 16, of the cover 14, and the apertures 18, of the support frame 12.

The cover 14 is provided with a centrally located lens 19 in its front wall.

The lens 19 is a plano-convex lens.

The support frame 12 carries a central mirror system having a pair of mirrors 20.

Figure 2:
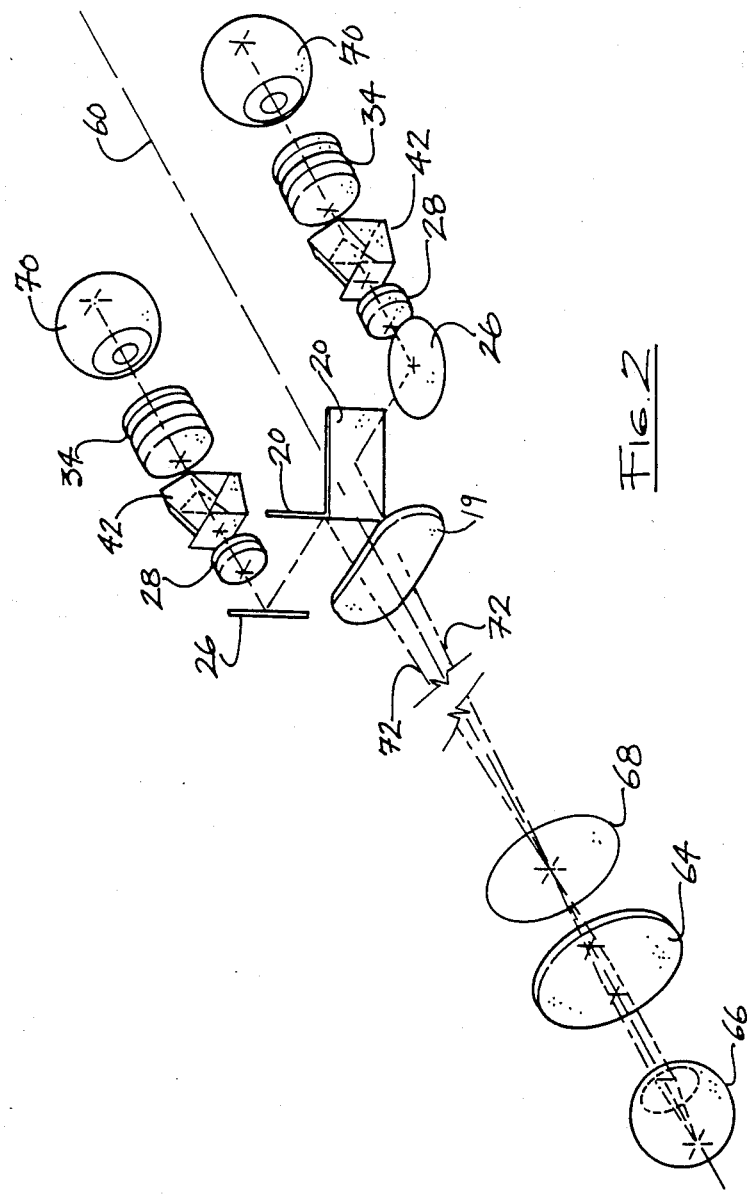
FIG. 2 is a perspective view of schematic form showing the lens system of the magnifying binocular ophthalmoscope shown in FIG. 1 in use with an ophthalmoscopy lens.

The reflective face of each mirror 20 is positioned at an angle of 135° to the optical axis 60 of the magnifying binocular ophthalmoscope 10. This is best seen in FIG. 2. The support frame 12 has a pair of tubes 22 mounted thereon. Each of the tubes 22 has an aperture 24 in its side wall. A mirror 26 is mounted in each of the tubes 22. Each of the mirrors 26 has its reflective face opposed to the reflective face of the nearer one of the two mirrors 20. Further, each mirror 26 is mounted such that its reflective face is parallel to the reflective face of its opposed mirror 20. Thus, the reflective face of each mirror 26 is positioned at an angle of 45° to the optical axis 60 of the magnifying binocular ophthalmoscope 10.

Each mirror 26 is mounted in its respective tube 22 such that its angle of rotation is adjustable. Thus, in the event that a mirror 26 becomes misaligned, realignment thereof is possible.

The central mirror system comprising the mirrors 20 is movable over a short distance, e.g. about 3 mm, in a direction parallel to the optical axis 60 of the magnifying binocular ophthalmoscope 10. This may be done by pushing or pulling the knob 44 of the shaft 46. This alters the length of the stereo base of the magnifying binocular ophthalmoscope 10.

Figure 4:
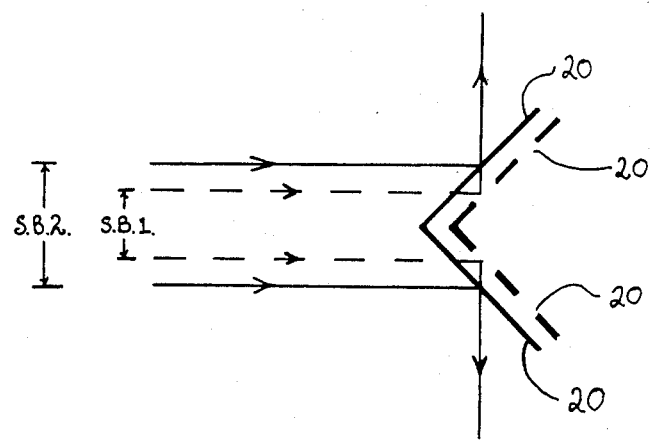
FIG. 4 shows the forward and rear positions of the central mirror system and how they change the stereo base.

This can be seen in FIG. 4, in which the central mirror system is shown in its forward position by solid lines and in its rear position by the broken lines.

In the forward position of the central mirror system the stereo base S.B.1. is longer than the stereo base S.B.2. in the rear position of the central mirror system.

Each of the tubes 22 contains the magnification system of the magnifying binocular ophthalmoscope 10.

The magnification system may comprise a Kepler telescopic system.

The Kepler system is preferred over other telescopic systems, e.g. the Galilean, because it is able to achieve higher magnification of good quality, which is more distinct in the peripheral field of view, compared with, for example, the Galilean system. This is due, essentially, to the position of the exit pupil. (The exit pupil is the image of the objective lens projected through the eye-piece, in a telescopic system).

In the Kepler system, the exit pupil is projected in the pupil of the observer's eye. In the Galilean system, however, the exit pupil is projected somewhere in the middle of the lens system, away from the observer's eye.

Whilst the Kepler system is a longer telescopic system and also has an inverted image, these problems can be overcome by the use of a Schmidt or Pechan Prism.

Figure 3:
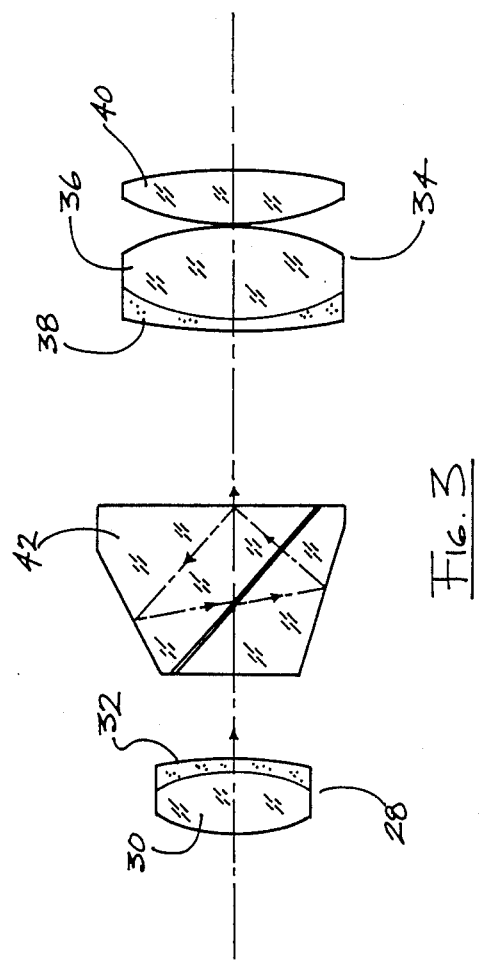
FIG. 3 is a schematic view of a magnification system, based on the Kepler telescopic system, for the magnifying binocular ophthalmoscope of the present invention.

A Kepler magnification system, suitable for the magnifying binocular ophthalmoscope 10, is shown in FIG. 3.

The objective lens 28 may comprise a cemented achromatic doublet composed of a positive crown glass element 30 and a negative flint glass element 32. Each element 30 and 32 would cancel the other's chromatic aberration.

The eye-piece 34, located at the end of each tube 22 remote from the mirrors 26, may comprise a cemented achromatic doublet composed of a positive crown glass element 36 and a negative flint glass element 38 in combination with an asymmetric bi-convex lens of crown glass 40.

A Schmidt or Pechan Prism 42 is located intermediate the objective lens 28 and the eye-piece 34. The Schmidt or Pechan prism 42 will shorten the length of the Kepler telescope by "folding" the rays of light within the prism 42 and will, at the same time, cause a re-inversion of the image without interfering with the optical axis.

Each of the tubes 22 is provided with a rotatable collar 48 to enable its eye-piece 34 to be rotated to compensate for ametropia in the observer. (The collar 48 is rotated clockwise to compensate for myopia, and counter-clockwise to compensate for hypermetropia).

The support frame 12 may also carry a light source housing 52. A light source, such as a 6 volt/10 watt halogen lamp, may be housed in the housing 52. The lamp is connected to a power source (not shown) via cable 62. The power source is clipped or otherwise attached to some part of the clothing, e.g. a belt, of the operator of the magnifying binocular ophthalmoscope 10.

To effectively concentrate light from the light source, a hemispherical reflector (not shown) may be mounted at the rear of the light source in the housing 52. The hemispherical reflector is arranged such that heat and light is reflected away from the operator.

To insulate the magnifying binocular ophthalmoscope 10 from heat conducted by the lamp housing 52, a laminated tufnol layer 54 may be positioned between the lamp housing 52 and the frame 12 of the magnifying binocular ophthalmoscope 10. (The shaft 46 used for altering the stereo base extends into the laminated layer 54 and is connected to the central mirror system comprising the mirrors 20. The layer 54 may be of 3.1 mm thickness).

A single plano-convex condensing lens 56 is positioned at the front of the light source.

The optical axis of the light source housing 52 is situated parallel to, and above, the optical axis 60 of the magnifying binocular ophthalmoscope 10.

A prism (not shown) may be incorporated in the condensing lens 56 to direct the illumination beam from the higher disposed light source housing 52 to the lower disposed level of the optical axis 60. The illumination beam will then be refracted downwards by this prism to intersect the optical axis 60.

To reduce the discomfort and danger of concentration of light and infra-red radiation in the anterior part and retina of the patient's eye, an infra-red absorption filter may be placed between the light source in the light source housing 52 and the condensing lens 56.

The magnifying binocular ophthalmoscope 10 may be mounted on a frame, such as a conventional spectacles type frame, by way of a ball-joint. The ball-joint would enable the magnifying binocular ophthalmoscope 10 to be properly adjusted in front of the operators eyes.

In use, the magnifying binocular ophthalmoscope 10 is used with an ophthalmoscopy lens 64, as shown in FIG. 2. The light source in the light source housing 52 is energized and directed into the pupil of the eye 66 of the patient. An ophthalmoscopy lens 64 is placed in front of the eye 66 of a patient. The ophthalmoscopy lens 64 produces an aerial image 68 of the retina of the eye 66.

An observer, i.e. the operator of the magnifying binocular ophthalmoscope 10, then uses the magnifying binocular ophthalmoscope 10 to view and magnify the aerial image 68. The distance of the observer's eyes 70 to the ophthalmoscopy lens 64 will depend upon the power of the ophthalmoscopy lens 64, but would generally be in the range of 25 cm to 50 cm.

To achieve binocular observation of a patient's retina, it is necessary that the placement of the image of the light source, in the light source housing 52, and the placement of the apertures of the telescopic system are within the pupil of the eye 66 of the patient.

FIG. 2 shows the light paths 72 from the retina of a patient's eye 66.

The light paths 72 pass through the lens 19 and strike the mirrors 20 of the central mirror system and are reflected onto the mirrors 26. The focal point of the lens 19 will approximately coincide with aerial image 68. From the mirrors 26, the light paths 72 pass through the telescopic system of the magnifying binocular ophthalmoscope 10. The observer's eyes 70 are placed adjacent the eye-pieces 34 and view a magnified aerial image 68.

The ability to alter the stereo base, by way of the knob 44 carried on the end of shaft 46, is particularly useful for observing the patient's peripheral retina.

When the patient looks to the left or to the right, his pupil appears as a vertically elongated oval, i.e. of elliptical shape, to the observer. The viewing and illuminating beams of the magnifying binocular ophthalmoscope 10 must fit within the elliptical shape of the patient's pupil.

If the patient looks to the left or to the right, to allow the observer a view of the 3 o'clock and 9 o'clock peripheral retina, it will be easier for both apertures of the viewing beams to pass through the smaller elliptical pupil shape by bringing both apertures closer together, and decreasing the stereopsis angle. This is done by pushing in the knob 44. This position is shown in FIG. 4 in broken lines with the stereo base being S.B.1.

In viewing the 6 o'clock and 9 o'clock peripheral retina, however, the pupil becomes horizontally elongated, and the images of both viewing and illuminating beams will not fit within this shape. In this case, indirect binocular ophthalmoscopy of the peripheral retina is much facilitated if the patient is reclined and looking upward, and the observer can then move around the patient, and is able to position himself to obtain the best peripheral view.

Preferably, the stereo base S.B.1. is 14 mm and the stereo base S.B.2. is 8 mm, with the distance D between the forward and rear positions of the central mirror system being 3 mm. The stereo base S.B.2. of 8 mm is determined by the diameter of the objective lens 28. The stereo base S.B.2. cannot be smaller than the diameter of the objective lens 28. Any attempt to reduce the stereo base S.B.2. will result in the apertures of both telescopic systems interfering with each other, and the field of view will be cut off by the central mirror system.

The field of view of the magnifying binocular ophthalmoscope 10 should be somewhat larger than the diameter of the ophthalmoscopy lens 64. This allows for flexibility in the alignment of the magnifying binocular ophthalmoscope 10 and the ophthalmoscopy lens 64. Additionally, it allows the observer some field to move around in.

An example of suitable powers for the lenses of the magnifying binocular ophthalmoscope 10 follows.

The plano-convex lens 19 has a power of +3.0 dioptres. The achromatic doublet 28 may have a total combined power of 32 dioptres and a lens aperture, i.e. diameter, of 8 mm. The total power of the eye-piece 34 may be +88 dioptres with a lens aperture of 12 mm.

The magnification at infinity of such a telescopic system is given by:

$$\text{MAGNIFICATION} = +88/+32 = 2.75$$

$$\text{DIAMETER OF EXIT PUPIL} = +8mm/2.75 = 2.9 \text{ m}$$

The pupil diameter of the observer's eye 70 should always be larger than 2.9 mm to experience optimum brightness of the telescopic system of the magnifying binocular ophthalmoscope 10.

The telescopic system of the magnifying binocular ophthalmoscope 10 is not used at infinity but at a working distance of 25–40 cm, the distance at which the aerial image 68 is observed.

Adjustment of the telescopic system of the magnifying binocular ophthalmoscope 10 at a shorter working distance may be achieved by turning out the collars 48, carrying the eye-pieces 34, which increases the distance between the objective lens 28 and the eye-piece 34.

In order for the telescopic system of the magnifying binocular ophthalmoscope 10 to focus at an aerial image 68, that is located 25 cm in front of the objective lens 28, 4 dioptres should be deducted from the power of the objective lens 28, leaving a power of 28 dioptres.

The magnification at a 25 cm working distance is given by:

$$\text{MAGNIFICATION} = +88/+24 = 3.14$$

Since 25 cm is the working distance to which magnification is normally compared, no further magnification is added. In order for the telescopic system of the magnifying binocular ophthalmoscope 10 to focus at an aerial image 68 that is located 40 cm in front of the objective lens 28, 2.5 dioptres should be deducted from the power of the objective lens, leaving a power of 29.5 dioptres.

The magnification at a 40 cm working distance is given by:

$$\text{MAGNIFICATION} = +88/29.5 = 2.98$$

Since 25 cm is the working distance to which magnification is normally compared, a magnification correction of 25 cm/40 cm = 0.625 is applicable, leaving a total magnification at $0.625 \times 2.98 = 1.86$.

The condensing lens 56 may have a power of +40 dioptres and a diameter of 15 mm.

The present invention allows for enhanced viewing of a patient's retina by an observer, such as an ophthalmologist, by providing a magnification of the aerial image of the retina produced by an ophthalmoscopy lens.

Modifications and variations such as would be apparent to a skilled addressee are deemed within the scope of the present invention.

I claim:

1. A magnifying binocular ophthalmoscope for use with an ophthalmoscopy lens to magnify an incoming image entering said ophthalmoscope, said ophthalmoscope comprising:

a light source housing containing a light source for illuminating the interior of a patient's eye;

mirror means and two image reflection means;

said mirror means having two mirror units arranged to reflect said incoming image into two paths;

each said image reflecting means being arranged to receive and reflect said incoming image from a respective said path;

each said image reflecting means reflecting said incoming image through a respective magnifying lens system comprising on objective lens, a Schmidt or Pechan prism and an eye-piece through which an observer views a magnified incoming image, and each magnifying lens system has an optical axis; wherein, each said image reflecting means, objective lens, Schmidt or Pechan prism and eye-piece are linearly aligned whereby each said optical axis is a single non-deviating line extending from a respective said image reflecting means to a respective said eye-piece and whereby the said optical axes are parallel.

2. A magnifying binocular ophthalmoscope in accordance with claim 1, wherein said Schmidt or Pechan prism is located between said objective lens and said eye-piece.

3. A magnifying binocular ophthalmoscope in accordance with claim 1, wherein said two image reflecting means comprise two further mirror units.

4. A magnifying binocular ophthalmoscope in accordance with claim 1, wherein said two mirror units of said mirror means are at substantially a right angle to one another and a plano-convex lens is positioned forward of said mirror means such that said incoming image is refracted by said plano-convex lens prior to said incoming image impinging upon said two mirror units of said mirror means.

* * * * *

UNITED STATES PATENT AND TRADEMARK OFFICE
CERTIFICATE OF CORRECTION

PATENT NO. : 4,838,678
DATED : June 13, 1989
INVENTOR(S) : Maximiliaan Joseph Hubertus Cuypers It is certified that error appears in the above-identified patent and that said Letters Patent is hereby corrected as shown below:

On the title Page:

Change inventor's name from "Maximiliaan J. Hubertus" to -- Maximiliaan Joseph Hubertus Cuypers --.

Change assignee from "Lyons Eye Institute of Western Australian Incorporated" to -- The Lions Eye Institute of Western Australia Incorporated --.

In the Abstract: Line 1, change "opthalmoscope" to -- ophthalmoscope --.
Line 7, change "opthalmoscope" to -- ophthalmoscope --.

Column 6, line 5, Claim 1, change "reflection" to -- reflecting --

Signed and Sealed this

Third Day of April, 1990

Attest:

HARRY F. MANBECK, JR.

*Attesting Officer*　　　　*Commissioner of Patents and Trademarks*